(12) United States Patent
Elsheikh et al.

(10) Patent No.: US 9,247,877 B2
(45) Date of Patent: Feb. 2, 2016

(54) DEVICE FOR MONITORING INTRAOCULAR PRESSURE

(75) Inventors: Ahmed Elsheikh, Liverpool (GB); John Clamp, Cambridge (GB)

(73) Assignees: UNIVERSITY OF DUNDEE (GB); CONTACT LENS PRECISION LABORATORIES LTD (GB)

(\*) Notice: Subject to any disclaimer, the term of this patent is extended or adjusted under 35 U.S.C. 154(b) by 133 days.

(21) Appl. No.: 13/823,031

(22) PCT Filed: Oct. 20, 2011

(86) PCT No.: PCT/GB2011/052032
§ 371 (c)(1),
(2), (4) Date: Mar. 13, 2013

(87) PCT Pub. No.: WO2012/052765
PCT Pub. Date: Apr. 26, 2012

(65) Prior Publication Data
US 2013/0184554 A1    Jul. 18, 2013

(30) Foreign Application Priority Data
Oct. 20, 2010  (GB) .................................. 1017637.8

(51) Int. Cl.
*A61B 3/16*   (2006.01)

(52) U.S. Cl.
CPC ........................ *A61B 3/16* (2013.01)

(58) Field of Classification Search
CPC ....................................................... A61B 3/16
USPC .................. 600/398, 405, 587, 561
See application file for complete search history.

(56) References Cited

U.S. PATENT DOCUMENTS

| | | | |
|---|---|---|---|
| 4,089,329 A | 5/1978 | Couvillon, Jr. et al. | |
| 4,305,399 A | 12/1981 | Beale | |
| 4,922,913 A | 5/1990 | Waters, Jr. et al. | |
| 5,179,953 A | 1/1993 | Kursar | |
| 7,137,952 B2* | 11/2006 | Leonardi et al. | 600/398 |
| 2002/0193674 A1 | 12/2002 | Fleischman et al. | |
| 2004/0186366 A1 | 9/2004 | Leonardi et al. | |
| 2007/0129623 A1 | 6/2007 | Fleischman et al. | |
| 2011/0184271 A1 | 7/2011 | Veciana et al. | |

FOREIGN PATENT DOCUMENTS

| | | |
|---|---|---|
| CN | 100998496 A | 7/2007 |
| EP | 0 061 777 A2 | 10/1982 |

(Continued)

OTHER PUBLICATIONS

The International Preliminary Report on Patentability and Written Opinion dated May 2, 2013 issued in corresponding International Application No. PCT/GB2011/052032.

(Continued)

*Primary Examiner* — Brian Szmal
(74) *Attorney, Agent, or Firm* — Ostrolenk Faber LLP

(57) ABSTRACT

Disclosed is a device adapted to measure intraocular pressure comprising: a corneal contact lens having a pressure sensor mounted in a recess or cavity in the contact lens, and wherein the contact lens has a back surface which is formed so as to protrude in a desired portion beyond the profile of the adjacent part of the lens and thus to press against the cornea, which protruding portion experiences a reactive deformation which is detected directly or indirectly by the pressure sensor.

42 Claims, 10 Drawing Sheets

(56) References Cited

FOREIGN PATENT DOCUMENTS

| WO | WO 03/001991 A1 | 1/2003 |
|---|---|---|
| WO | WO 2007/136993 A1 | 11/2007 |
| WO | WO 2008/101374 A2 | 8/2008 |
| WO | WO 2009/147277 A1 | 12/2009 |
| WO | WO 2010/061207 A1 | 6/2010 |

OTHER PUBLICATIONS

International Search Report dated Jun. 22, 2012 issued in corresponding International patent application No. PCT/GB2011/052032.
Leonardi, Matteo et al.: "Wireless contact lens sensor for intraocular pressure monitoring: assessment on enucleated pig eyes.", Acta Ophthalmologica Jun. 2009 LNKD-PUBMED: 19016660, vol. 87, No. 4, pp. 433-437, XP002665763.
Twa, Michael D. et al.: "Evaluation of a contact lens-embedded sensor for intraocular pressure measurement.", NIH Public Access Author Manuscript, Journal of Glaucoma, Aug. 2, 2010, pp. 1-23, XP002665764.
Matteo Leonardi et al., "First Steps toward Noninvasive Intraocular Pressure Monitoring with a Sensing Contact Lens", *Investigative Ophthalmology & Visual Science*, 45(9):3113-3117 (Sep. 2004).
Office Action dated Jan. 22, 2015 and Search Report in corresponding Chinese Patent Application No. 201180050570.6 (with English language translation)(8 pages).

* cited by examiner

DEVICE FOR MONITORING INTRAOCULAR PRESSURE

CROSS REFERENCE TO RELATED APPLICATIONS

The present application is a 35 U.S.C. §371 National Phase conversion of PCT/GB2011/052032, filed Oct. 20, 2011, which claims benefit of United Kingdom Application No. 1017637.8, filed Oct. 20, 2010, the disclosure of which is incorporated herein by reference. The PCT International Application was published in the English language.

This invention relates, inter alia, to a contact lens device for the measurement and/or continuous monitoring of intraocular pressure, to apparatus comprising the device, and a method of measuring or monitoring intraocular pressure using the device or apparatus.

BACKGROUND

Glaucoma is a group of diseases of the eye which, worldwide, is among the leading causes of irreversible blindness. The major risk predictor for the diseases is increased intraocular pressure (IOP). Therefore, risk profiling for, and management of, glaucoma includes measurements of IOP via tonometry.

It is generally accepted that the normal range of IOP is 10 to 21 mmHg, and individuals with an IOP higher than this range will usually take IOP lowering medication to prevent or delay the progression of glaucoma. Also, IOP for the individual can vary throughout a 24 hour period depending on whether the individual is asleep or awake, the level of physical exertion or hydration, and the psychological state. Therefore, measuring IOP only during irregular daytime periods, such as during two or three clinic visits a year, does not provide sufficient information for proper management of the disease.

A common method of measuring IOP is applanation tonometry which measures IOP whilst flattening a constant area of the cornea using a solid surface applied to the cornea. Since contact is made with the cornea, an anaesthetic must be introduced onto the surface of the eye. Apart from the discomfort for the subject, clinical technicians are required to take the measurements. This also entails that measurements will be taken only during the daytime office hours, which does not capture the natural variation of IOP and its increase during sleep and does not provide sufficient information for proper management of glaucoma. Other methods of measuring IOP exist which involve non-contact tonometry, but these suffer from the same or other disadvantages.

Furthermore, all pressure measurement devices (contact and non-contact) used to measure IOP are affected to different extents by the stiffness of the cornea. Thus, for example, a cornea with high stiffness, caused e.g. by high thickness or rigid tissue, would lead to an overestimation of IOP, and could result in a false positive diagnosis of glaucoma. Corneal stiffness varies from individual to individual due to variations in factors including thickness, curvature, age and medical history. Therefore, measured values of IOP require correction or calibration to account for these natural variations in stiffness.

The IOP varies with systemic blood pressure, such that there is an oscillating variation in IOP, termed the "ocular pulse amplitude" (OPA), which is defined as the difference between the maximum and minimum values of the ocular pulse wave. The OPA is of interest in management of glaucoma, since it provides a measure of the pressure range to which the eye is subjected. Recent studies suggest significantly higher OPA values in the eyes of glaucoma patients than in the eyes of healthy subjects.

It is desirable to provide a device for measuring IOP which substantially avoids discomfort for the subject or the need for clinical technicians and the like to perform the measuring process.

It is desirable to provide a device for measuring IOP which allows multiple measurements to be taken over at least a 24 hour period. It is also desirable to provide a device for measuring IOP which allows substantially continuous measurements to be taken. It is further desirable to measure OPA and its variation profile over at least a 24 hour period. It is also further desirable to eliminate the effect of corneal stiffness on IOP measurements to improve the accuracy of IOP output and remove the need for calibrating the tonometry device for every patient.

It is known that the cornea changes in structure as the distance from the centre of the cornea increases. In a central region, up to a diameter of approximately 7 mm, the cornea includes collagen fibrils which predominately have a vertical or horizontal orientation. In an outer region beyond this, starting from a diameter of about 11 mm, the collagen fibrils have a predominantly circumferential orientation. It has been found that the transitional region, having a diameter from about 7 to about 11 mm, between the central region and the outer region is characterised as being an area of low stiffness. Therefore, deformations in the cornea due to changes in IOP will be most apparent at this location, and in the radial direction.

It is known (e.g. U.S. Pat. No. 5,179,953; U.S. Pat. No. 4,089,329) to provide a semi-rigid ring or contact lens which applanates the sclera of the eye and holds a pressure sensor such as a strain gauge in contact with the sclera to measure IOP. Due to the requirement to cause applanation of the naturally stiff sclera, these devices are bulky and uncomfortable to wear. Other techniques rely on the use of corneal contact lenses equipped with pressure sensors, but these either measure IOP at a single point and require patient activation (US 2007/0129623), or measure IOP with circumferential pressure sensors, the placement of which is based on the geometric form of the cornea without consideration of the cornea's microstructure and its particularly low stiffness at the transition region and in the radial direction (WO 03/001991).

It is desirable to provide a device which measures IOP and/or OPA at or near the transitional region of the cornea. It is desirable to provide a device for measuring IOP which avoids causing patient discomfort and avoids obstructing the vision of the subject.

In published patent application WO 2010/061207 there is described a device which seeks to meet some of these requirements and which discloses various embodiments of a contact lens having an in-built pressure sensor.

It has been found that further improvements can be made which increase the accuracy and consistency with which the device interacts with the cornea and assesses intraocular pressure.

SUMMARY OF THE INVENTION

According to the present invention there is provided in a first aspect a device adapted to measure intraocular pressure comprising:

a corneal contact "lens" having a pressure sensor mounted in a recess or cavity in the contact lens, and wherein the contact lens has a back surface which is formed so as to protrude in a desired portion beyond the profile of the adjacent part of the lens and thus to press against the cornea, which protruding portion experiences a reactive deformation which is detected directly or indirectly by the pressure sensor.

Typically the protruding portion experiences a reactive deformation (caused by the cornea pushing back against the contact lens) when the eyelids are closed, but substantially no deformation when the eyelids are open. Thus, for example, the protruding portion may undergo a reactive deformation transiently, during blinking, or over a more prolonged period if the subject is asleep.

The protruding portion of the lens is formed on the back surface, whilst conveniently the front surface of the lens is formed with a recessed section. Conveniently the protruding portion underlies the recess or cavity section of the contact lens. Advantageously, the protruding portion, the recess or cavity in the contact lens, and at least one component of the pressure sensor, will all be configured so as generally to overlie the transitional region of the cornea when the contact lens is correctly positioned on the subject's eye.

Preferably the recess or cavity section of the contact lens has relatively weakened edges to assist in deformation thereof under eyelid pressure. The relative weakening is typically effected by making the edge or a peripheral region of the recess or cavity section relatively thin, so that they can act as a 'hinge', allowing the lens to deform. In some embodiments the peripheral region of the recess or cavity section of the lens is in the range 25-50 μm in thickness, more preferably 30-40 μm thick. In contrast, the main body of the lens will conveniently have a thickness in the range 120-250 μm.

The recess or cavity section of the contact lens may also have a narrow weakened centre section to further assist in deformation under eyelid pressure, thus increasing the sensitivity of the device.

In preferred embodiments the recess or cavity section of the contact lens accommodates a stiff bridge portion or member, which has an elastic modulus E, which is greater than that of the contact lens material. Preferably the elastic modulus of the bridge portion is at least 100 times greater than that of the contact lens material, more preferably 200-1000 times greater, and most preferably about 500 to 1000 times greater.

Whilst the stiff bridge member needs to be rigid enough to protect the associated electronics, and avoid deformation under the pressure exerted by the eyelids, it should also conveniently have enough flexibility to allow for some deformation during fitting to the contact lens, and to reduce the likelihood of damage if the component is subjected to impact.

In one embodiment, the stiff 'bridge' member will be formed with an elastic modulus, E, in the range 300 MPa to 3 GPa, more preferably in the range 500 MPa to 3 GPa.

Materials suitable for use in manufacture of the stiff bridge member will be non-toxic and biocompatible, with a sufficiently high rigidity. Many synthetic plastics materials possess the requisite properties, and the following is a non-exhaustive list: Perspex, acetal, polyurethane, polypropylene, polyvinyl chloride, high density polyethylene (HDPE), polyamide (nylon), and polyether ether ketone (PEEK).

Conveniently, the bridge member bridges over the recess or cavity in the lens so as to provide a smooth continuation of the profile of the front surface of the lens (i.e. that surface which is further from the cornea when the lens is being worn), otherwise a sharp discontinuity in the profile of the lens as a result of the formation of the recess or cavity would be likely to cause irritation or discomfort to a wearer of the lens. Thus, once the bridge member is positioned on the lens, the front surface of the lens presents a generally smooth profile.

The bridge portion will usually be circular (more especially, annular) or arcuate, so as to be accommodated within the correspondingly shaped recess or cavity section.

The main function of the stiff bridge member is to transfer pressure from the eyelid or eyelids, when closed or closing, to the protruding portion of the contact lens (and hence to the cornea). To assist in this, it may be desirable for the bridge portion to have one or more feet which bear on a peripheral region of the recessed or cavity section of the lens, which peripheral region will advantageously be thinner than the main body of the contact lens, so as to act as a hinge.

As described in detail elsewhere, desirably the pressure sensor will comprise at least one component mounted on, incorporated within, or otherwise attached to, the bridge portion. In a preferred embodiment the pressure sensor comprises a capacitor, one of the 'plates' of which is mounted on, incorporated within, or otherwise attached to the bridge portion.

It is further preferred that the device of the invention will comprise a diaphragm member or component. The diaphragm member or component will desirably have an elastic modulus, E, which is intermediate in value between that of the relatively soft contact lens and that of the relatively stiff bridge portion. Conveniently the elastic modulus E of the diaphragm will be in the range 20 to 40 times greater than that of the contact lens material. Typical values of E for the diaphragm are in the range 1 MPa to 40 MPa, more typically 1-20 MPa, depending on the thickness. Thus, for example, a diaphragm with a thickness of 10 μm would typically have a modulus of about 40 MPa, whilst a diaphragm 40 μm thick would have a modulus of about 10 MPa. Materials suitable for use in manufacturing the diaphragm include silicone-rubber-based materials and other rubber and rubber-composite-based materials (e.g. polyvinyl siloxane).

The diaphragm is typically located within the recessed or cavity section of the contact lens, and is correspondingly sized and shaped. More especially, the diaphragm is preferably positioned overlying the protruding portion of the contact lens. In particular the diaphragm is desirably positioned overlying the protruding portion of the lens and beneath, but generally apart from, the bridge member.

The bridge member will typically however have one or more legs or supports which bear on the diaphragm, as explained in greater detail elsewhere. The bridge member may be retained in the recess or cavity section of the contact lens by a frictional e.g. dove-tail fit, and/or by use of an adhesive. Suitable adhesives include silicone-based glues, such as "Silicoset 158", made by ACC Silicones Ltd., Bridgewater, UK. In some embodiments, the legs or supports of the bridge member are glued to the diaphragm, at the edges thereof. The diaphragm itself may, if desired, be glued (e.g. using a similar silicone-based adhesive) to the contact lens.

In a preferred embodiment, a capacitor 'plate' forming part of the pressure sensor is mounted on, incorporated within, or otherwise attached to, the diaphragm. The separation between the diaphragm and the bridge member can accommodate the dielectric of the capacitor. The dielectric may most conveniently comprise air or other gas, but in principle some other relatively electrically insulating substance may be used.

The diaphragm, being more rigid than the contact lens material, helps to press the protruding portion of the lens against the cornea. The diaphragm, being immediately adjacent to/in contact with, the contact lens will be subject to the reactive deformation of the lens.

The pressure sensor typically comprises means for measuring or monitoring the amount of reactive deformation of the diaphragm, thus enabling calculation or derivation of the IOP (e.g. via a digital look-up table or from stored values in an electronic memory device).

In one embodiment, the contact lens comprises a recessed section in the form of a groove or channel, which may conveniently be square or rectangular in transverse section but can, in principle, have any shape section. The recess or cavity section may be circular (more especially, annular), running around the lens through 360°, or may be arcuate. If the recess or cavity section is arcuate, it will normally be preferred that it describes part of the circumference of a circle e.g. through a sector of between, typically, 75 to 285°, more preferably between 90 and 270°. If the recess or cavity section is less than a complete circle, the ends of the groove or channel of the recessed section will desirably taper so as to blend smoothly into the front surface of the lens, to avoid any sudden discontinuity, which might cause discomfort to a person wearing the contact lens.

In those embodiments in which the recess or cavity section is arcuate, it is preferred that, when worn on the eye of a subject, the recess or cavity section is located within the lower half of the lens. In order to accomplish this, it will be desirable that the lens is provided with some orientation means, which functions to retain the lens in the desired orientation on the eye. Suitable orientation means are well known to those skilled in the art and include one or more "wedges" or the like, which are conveniently provided on the front surface of the lens and/or around the lower periphery of the lens. An alternative solution is to make the lens prismatic, so that it is thicker at the bottom than the top.

The recess or cavity section, in which the bridge member is preferably accommodated, will preferably be positioned such that, when the lens is worn by a subject, the protruding portion and/or the recess or cavity section (and hence the associated pressure sensor) will overlie the transitional zone, which is located in a ring of from about 7 to about 11 mm diameter around the centre of the pupil. More especially the protruding portion and/or the pressure sensor is preferably substantially entirely located to overlie the cornea within the limits of the transitional zone. The transitional zone is believed by the inventors to be especially sensitive to changes in IOP, undergoing maximal displacements (compared to other parts of the cornea) in response to alterations in IOP. In addition, this arrangement leaves the central 6-7 mm diameter circle of the cornea unobstructed, so that the vision of the subject is substantially unimpaired by wearing the contact lens of the invention.

The contact lens may be a corrective lens (i.e. have some optical power selected so as to ameliorate a vision defect in the eye of the subject), but more usually will simply be a plano lens, without any optical power.

Accordingly, although the device of the invention contacting the cornea is referred to as comprising a contact lens, it will be understood that the 'lens' may not have all the optical properties of a lens, and the term 'lens' as used herein is accordingly not to be construed strictly unless the context dictates otherwise. As well as the possibility of being a zero power 'plano' lens, there may also be embodiments in which the centre of the device, which overlies the middle part of the eye of the subject, is omitted or a central aperture is formed in the device. Thus, for example, the device may be substantially annular in shape, with e.g. a substantially circular aperture surrounded by a circumferential ring. Such an embodiment has certain advantages, described further below.

It is a feature of preferred embodiments of the device of the invention that either: the portion of the device which overlies the central part of the subject's cornea (e.g. a centrally positioned circle with a diameter of about 6 mm) is substantially transparent; or a central aperture is provided in the device. In either instance, the effect is that the wearing of the device on the subject's eye is not significantly detrimental to the subject's uncorrected vision. This is in contrast to some prior art devices, which contain opaque elements overlying the centre of the subject's cornea such that, when used, the device completely blocks, or is significantly detrimental to, the subject's vision in that eye.

In one embodiment the device of the invention has a central aperture which is essentially circular, typically of about 3-5 mm in diameter. Embodiments in which an aperture is provided in the device have, as described above, the advantage that they do not impede the subject's unaided vision in the eye concerned. However they also possess other advantages. The presence of the aperture allows unimpeded oxygen flow to the cornea, which is especially desirable if the device is to be worn for extended periods (e.g. overnight), since lack of oxygen flow to the cornea can cause significant discomfort. A further significant advantage is that the presence of an aperture allows for the use of an applanation tonometer, such as a Goldmann applanation tonometer, whilst the device is in situ on the cornea. The applanation tonometer can be used to measure the intraocular pressure and thereby allow direct calibration of the measurements obtained using the device of the invention against IOP determinations made using accepted conventional techniques. This offers a very easy method of calibrating the device of the invention.

In a preferred embodiment, the contact lens of the invention will comprise a pressure sensor which has a capacitive and/or inductive transducer element.

In a typical embodiment, the pressure sensor will comprise two electrically conducting elements which are separated by a gap or dielectric, and thus are capable of acting as a capacitor. The dielectric is typically air or another gas, but could be silicone or a hydrogel. The conducting elements may comprise thin wires (e.g. copper or gold) or thin metal membranes, or may comprise a transparent conductive indium/tin oxide (ITO) thin film. Metals are of course generally good electrical conductors and so may be preferred, but other substances could in principle be used to fabricate the conducting elements, and are not excluded.

Typically one of the conducting elements moves in response to changes in IOP, such that the relative separation between the conducting elements alters, thereby altering the capacitance of the system. Advantageously, one of the conducting elements is supported on the diaphragm which experiences reactive deformation with changes in IOP. Advantageously, the other conducting element is supported on the relatively rigid bridge member. Thus the relative separation of the conducting elements alters with IOP. It is however conceivable that the other conducting element is positioned elsewhere on the contact lens (i.e. not on the bridge member). The two conducting elements may be described as the 'plates' of a capacitor, although it will be appreciated that the term 'plate' is used in this context as a function term, rather than describing the appearance of the conducting elements.

A further preferred feature of the lens of the invention is the inclusion of responder coil. This may be situated, in theory, anywhere on the lens but must be sufficiently close to be in operable linkage with at least one of the conducting elements. Preferably therefore the responder coil is on or in the bridge member. The responder coil is typically comprised of thin metallic wire, such as gold, copper or the like. The responder coil is typically an annular coil, substantially co-axial with the contact lens. The term "coil" as used herein, is not intended necessarily to limit the responder coil to a particular physical shape but it intended to indicate that the component has an inductance when exposed to fluctuating electromagnetic field. Nevertheless, a helical coil is a preferred shape for the responder coil.

The responder coil may preferably be subjected to a fluctuating magnetic field by the use of an exciter coil, positioned sufficiently close to the responder coil. The exciter coil is preferably substantially co-axial with the responder coil.

Accordingly, the device of the first aspect of the invention may conveniently be provided in a kit or in combination with an external instrument, which external instrument comprises an exciter coil which can be positioned so as to excite a responder coil provided on the device. In a preferred embodiment, an exciter coil is provided on a pair of spectacles worn by the subject. The spectacles typically comprise two corrective lenses appropriate to correct or ameliorate a vision defect in the subject, but they could alternatively comprise one or two planar lenses. In a preferred embodiment, the exciter coil is placed on the lens or lenses of the spectacles, more particularly, on the rear surface of the lens or lenses (i.e. that surface nearer to the subject's eye). The exciter coil is conveniently formed from a transparent conducting indium tin oxide (ITO) film or other similar material, so as not to interfere with the vision of the subject.

The external instrument preferably comprises other functional components, such as any one, two or more, or all, of the following: a source of electrical power to drive the exciter coil; a digital signal processing unit; a wireless, Bluetooth or other signal communication unit; and a data storage unit.

The source of electrical power will most conveniently be a battery, such as lithium battery, button cell etc., but in principle other sources might be used e.g. a photovoltaic cell, fuel cell, and so on.

A suitable arrangement of responder and exciter coils which may be useful in the present arrangement is disclosed in WO 03/088867.

Although not necessary to understand and perform the invention, by way of explanation, the power source powers the exciter coil with an alternating current of varying frequency. Preferably the apparatus cycles through a range of AC frequencies. This creates a magnetic field which in turn induces an emf in the responder coil on the contact lens on the subject's eye. The combination of inductance and capacitance components on the contact lens creates a resonator. When the exciter coil causes the resonator to oscillate at its resonant frequency, there is an amplitude peak in the measured current flowing through the driving circuit on the spectacles. The resonant frequency of the resonator on the contact lens depends on the width of the gap between the conducting elements (effectively the 'plates' of the capacitor) on the contact lens, which in turn depends on the IOP. In this manner, a measure of the IOP can be obtained. It will be apparent to those skilled in the art that the resonant frequency of the oscillator can be detected in other ways (i.e. more generally, by measuring a relevant electrical characteristic), such as by measuring a voltage across a resistance or impedance in the driving circuit.

In one embodiment, the apparatus associated with the device may comprise:
  (a) a waveform generator chip (e.g. the Analog Devices Direct Digital Synthesizer Chip AD9951) to generate a waveform (e.g. sinusoidal wave) to energise the exciter coil; and
  (b) an analogue to digital converter (ADC) to measure the power within the exciter coil; and
  (c) a microprocessor or the like to control the waveform generator chip to produce e.g. about 100 discrete frequencies over a desired frequency range (e.g. 10 MHz to 200 MHz), each frequency being produced for a short time period (for example, about 10 milliseconds each), and to record the resulting response from the ADC.

Using this arrangement, a discontinuity in the response can be detected, which represents the resonant frequency of the system. The resonant frequency depends, in part, on the capacitance of the 'plates' in the pressure sensor, which itself depends on the deformation of the sensor, which is determined by the IOP.

It will be apparent that, in order to operate effectively, there must be a good functional inductive coupling between the responder and the exciter coils. The coupling constant, K, is a measure of the coupling between the coils, with a value of 1 representing 100% coupling. The value of K can be maximized by decreasing the separation between the coils, and by increasing the number of turns of one or both coils.

When a resonant frequency can no longer be detected by the apparatus, data can no longer be obtained. A likely cause of this is a loss of effective coupling between the exciter and responder coils (e.g. because the spectacles have slipped). The apparatus preferably provides an audible and/or visible alarm when coupling is lost for longer than a predetermined time threshold (e.g. 10 seconds or 20 seconds). In order to reduce the likelihood of the spectacles slipping, they will preferably be shaped and sized to fit the subject closely, and/or may be provided with an elastic or resilient fitting means, such as a resiliently deformable band which passes from one arm of the spectacles, around the back of the subject's head, to the other arm of the spectacles.

An important feature of the present invention is that it can allow the acquisition of IOP data over at least a 24 hour period, including night time, and even when the subject is asleep. When the subject wishes to sleep, the spectacles can be removed, and replaced with an eye mask, which typically will be opaque. The eye mask will, like the spectacles, comprise an exciter coil to drive the responder coil. For improved comfort, it will probably be desirable that the rest of the apparatus (e.g. the electrical power source; digital signal processing unit; communication unit; data storage unit) be provided remotely, and the eye mask connected to a power source by a power lead etc. The use of the eye mask not only allows continued data acquisition whilst the subject is sleeping, but also provides especially good coupling to the responder coil, as the exciter coil can usually be positioned much closer to the responder coil than when it is mounted on spectacles.

In addition, since the contact lens can only sense IOP when it is pressed against the cornea by the action of the eyelids, it follows that, during daylight hours, readings can be obtained only when the subject blinks or closes their eyes for some other reason. This occurs frequently enough to provide good data (the average human adult will blink several times a minute, typically about 10 blinks per minute in a laboratory setting, about 3-4 blinks per minute when reading). At night, the subject's eyes will be closed essentially continuously for hours at a time. This allows the continuous monitoring of IOP by the apparatus of the invention and, in particular, allows measurement of OPA. For present purposes, measurement of OPA is considered to represent a particular embodiment of IOP, and in preferred embodiments, the device of the invention is capable of measuring and/or monitoring OPA, preferably over a period of at least 24 hours. The apparatus will advantageously be programmed with software written to enable extraction of the OPA profile from the data.

The device of the invention relies on eyelid closure (during blinking or in sleep) to press the device against the cornea and thus cause a reactive deformation. However, it is desirable that the measurements obtained using the device should be largely independent of the pressure created by the eyelids themselves, which in turn largely depends on the rigidity of the eyelids. The rigidity of the eyelids declines with age, as the eyelids lose elasticity. The inventors have investigated this and have found that the device of the invention has only low sensitivity to eyelid pressure, which is a highly desirable characteristic.

It will generally be preferred that the apparatus does not continuously take readings all the time that the contact lens is in place on the subject's eye. This is for two reasons. Firstly, although the amount of electromagnetic radiation to which a subject is exposed is not great, there might be possible concerns over a health-risk if the exposure is continuous and over prolonged periods. Secondly, the amount of energy consumed by the device can be reduced (and hence, for example, battery life extended) by utilizing discontinuous monitoring.

Thus for example, the apparatus may only be activated for say 10 seconds every 1 to 5 minutes, or thereabouts. A simple timer mechanism on the external unit will suffice to control the timed operation of the device. The timing may conveniently be made variable e.g. less frequently at night, when the subject is likely to be asleep and therefore there is a greater chance of obtaining a reading.

It will be apparent from the foregoing that, in preferred embodiments, the contact lens of the invention will be worn by the subject for prolonged periods, typically over at least 24 hour period, preferably over at least a 36 hour period. The lens should desirably therefore be suitable for use in these conditions without causing unacceptable discomfort to the subject. Accordingly, the lens will preferably have a high oxygen permeability, of at least $40 \times 10^{-11}$ cm$^2$ mL$_{O_2}$ / s mL mm$_{Hg}$, preferably at least $60 \times 10^{-11}$ cm$^2$ mL$_{O_2}$ / (s mL mm$_{Hg}$). The elastic modulus of the contact lens is conveniently in the range 0.1-0.5 MPa, more especially 0.2-0.35 MPa. Suitable contact lens materials are known to those skilled in the art and include, for example, vinyl pyrrolidone, HEMA, and silicon hydrogel materials.

A further unique feature of the present invention concerns the calibration of the IOP measuring device. Some sort of calibration is required to be able to determine how the resonant frequency values or other data obtained by the device equate to IOP since, for example, the same IOP may generate different deformations of the cornea in different subjects, depending on the age of the subject, the thickness and rigidity of the cornea, and so on.

In the calibration method of the invention, the subject will wear at least a first "calibration" contact lens, before wearing the "measurement" lens, which will typically be suitable for wear over a period of at least 24 hours. The calibration contact lens and the measurement contact lens will differ in some characteristic in a known manner, in order to allow the response of the subject's cornea to the different lenses to be compared and calibrated. In a preferred embodiment, the characteristic which differs between the calibration lens and the measurement lens will be the shape, and more especially the steepness of curvature, of the protruding portion of the contact lens.

As an illustrative embodiment, a first calibration lens, with a relatively steeply curved protruding portion, will be worn for a period of time long enough to obtain sufficient data (e.g. 5 minutes). The relatively steeply curved calibration lens may be relatively uncomfortable, and so should not be worn for very long. If desired, a second and even a third or fourth calibration lens may then be worn, each differing in a known manner in the relevant characteristic, from the other calibration lenses (e.g. having successively more gently curved thickened portions). The subject is then provided with the measurement contact lens, which is sufficiently comfortable to be worn for a long period of time. The data acquired from the first and one or more subsequent lenses (whether further "calibration" lenses or the measurement lens) can be compared and, because the lenses differ from one another in a known manner, the mechanical response, and hence the elastic modulus (a measure of the stiffness) of the subject's cornea, can be obtained thus allowing calibration of the apparatus.

A particular advantage of this preferred method of calibration is that it measures the stiffness of the cornea directly. Conventional tonometry techniques to correct for varying corneal stiffness consider the effects of corneal parameters which influence the corneal stiffness, rather than directly measuring the corneal stiffness itself. Such parameters typically include corneal thickness and curvature.

Accordingly, in another aspect the invention provides a method of measuring or estimating corneal stiffness, the method comprising the steps of:

(a) introducing onto the eye of a subject a first device in accordance with the first aspect of the invention as hereinbefore defined, and obtaining a first data set relating to IOP in the subject's eye;

(b) removing the first device and introducing onto the same eye a second device in accordance with the first aspect of the invention, the second device differing in some relevant characteristic, in a known manner, from the first device, and obtaining a second data set relating to IOP in the subject's eye; and (c) comparing the first and second data sets to allow a measurement or estimation of the corneal stiffness of the subject's eye.

The method of this aspect of the invention can be used to calibrate the device and apparatus of the invention.

In a third aspect, the invention provides a method of directly calibrating a device in accordance with the first aspect of the invention, the method comprising the steps of:

(a) introducing onto the eye of a subject a device in accordance with the first aspect of the invention, wherein the device comprises a central aperture of sufficient dimension to permit the tip of an applanation tonometer to contact the cornea;

(b) obtaining measurements using the device of the first aspect;

(c) using an applanation tonometer to obtain one or more readings of IOP of the subject's eye whilst the device of the first aspect of the invention is in situ on the eye, by passing the tip of the applanation tonometer through the aperture, provided in the device, far enough to contact the cornea and obtain one or more IOP readings; and (d) directly calibrating the device using the measurements obtained in step (b) and the one or more readings of IOP obtained in step (c).

The applanation tonometer may conveniently be a Goldmann applanation tonometer. Desirably more than one reading of IOP is obtained in step (c), as this will allow calibration of the device over a range of IOP values. Advantageously, steps (b) and (c) will be performed either substantially simultaneously (although obviously not at exactly the same time, since the use of the applanation tonometer requires the eyelids to be open), and preferably within at least 10 minutes of one another, more preferably within 5 minutes, and most preferably within 3 minutes. It will be appreciated that step (c) may be performed before step (b), or vice versa. The calibration in step (d) may be performed in any convenient manner e.g.

using a programmable microprocessor device, modeling using finite element analysis of the cornea, or even graphically on paper.

In a fourth aspect, the invention provides a method of determining the IOP or OPA of a subject's eye, the method comprising the steps of:
(a) introducing onto the eye of the subject a device in accordance with the first aspect of the invention;
(b) obtaining at least one measurement using the device; and
(c) using the at least one measurement from (b) to determine the IOP or OPA of the subject's eye.

The subject is typically a human subject, especially one suspected of having glaucoma. Conveniently step (b) comprises obtaining a plurality of measurements. Desirably the measurements in step (b) are obtained over a period of at least 12 hours, more preferably over a period of at least 24 hours, so as to provide information about the IOP in the subject's eye over a significant period of time. In particular, the period in step (b) during which measurements are obtained advantageously comprises a period in which the subject is asleep (e.g. typically, overnight).

The measurements or estimations made using the method and apparatus of the invention are useful in detecting and diagnosing the onset or existence of glaucoma in a subject, indicated by abnormally elevated IOP or OPA readings.

In some embodiments the rigid bridge member may be separable from the contact lens and could be used in conjunction with different contact lenses. Accordingly the invention also encompasses a circular or arcuate stiff bridge member, preferably having an elastic modulus in the range 300 MPa to 3 GPa. The bridge member will advantageously further comprise a respondent coil as hereinbefore described. The coil will preferably be embedded within the bridge member.

The bridge member of the invention may also comprise a diaphragm, typically having the properties as hereinbefore described. The diaphragm may advantageously be adhered to the bridge member, preferably to the legs thereof, by a silicone-based adhesive.

The bridge member will preferably further comprise an electrically conducting element, such as a metallic membrane, which may act as one plate of a capacitor. A second capacitor plate will preferably be provided on the diaphragm.

For the avoidance of doubt it is hereby expressly stated that features described herein as "preferred", "advantageous", "convenient", "typical" or the like may be present in the invention in isolation, or in any combination with any one or more other such features so described, unless the context dictates otherwise. Furthermore, features so described in relation to one aspect of the invention are to be understood as applying equally to other aspects of the invention, unless the context dictates otherwise.

BRIEF DESCRIPTION OF THE DRAWINGS

These and other features of the invention will now be further described by way of illustrative embodiment and with reference to the accompanying drawings, in which.

DESCRIPTION OF PREFERRED EMBODIMENTS

EXAMPLES

Figure 1:
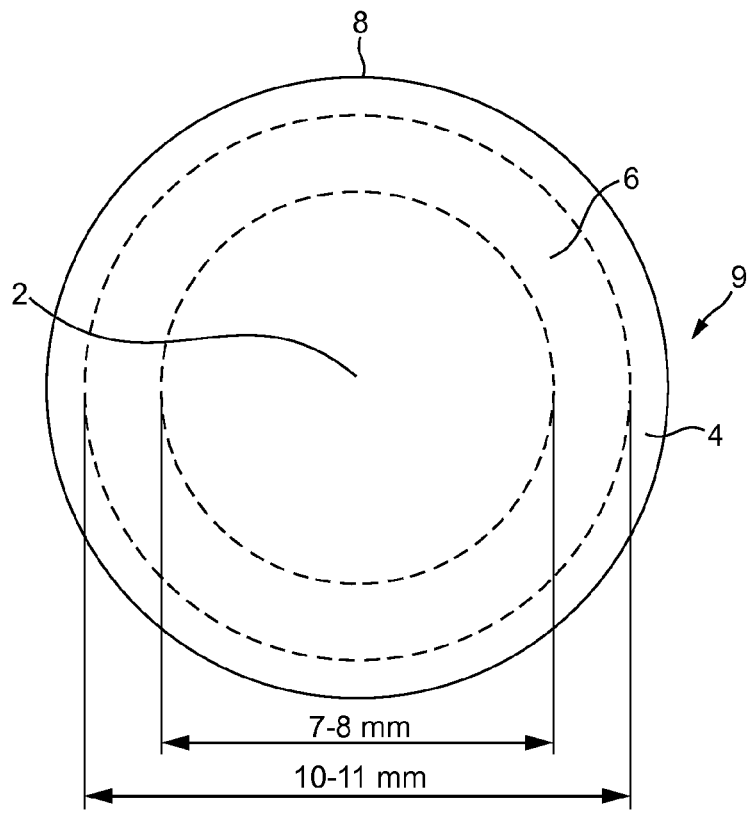
FIG. 1 is a schematic representation of a plan view of part of the typical human eye, showing the relative position and dimensions of the transitional region of the cornea.

Referring to FIG. 1, the cornea of the typical human eye has a central region, 2, with a diameter of about 7-8 mm. Within this central region, the collagen fibrils are predominantly arranged in the horizontal or vertical meridian directions. Further out is the circumferential region 4 which has a diameter starting at about 11 mm. In this region the collagen fibrils are arranged predominantly circumferentially. Between the central region 2, and the circumferential region 4, is the transitional region 6, which has a diameter of from about 7 or 8 mm to about 10 or 11 mm diameter. In this transitional region 6, the predominant direction of the collagen fibrils changes from horizontal/vertical to circumferential. Beyond the circumferential region 4, is the limbus 8, also known as the "corneo-scleral junction", which marks the inner edge of the sclera 9.

Example 1

Figure 2:
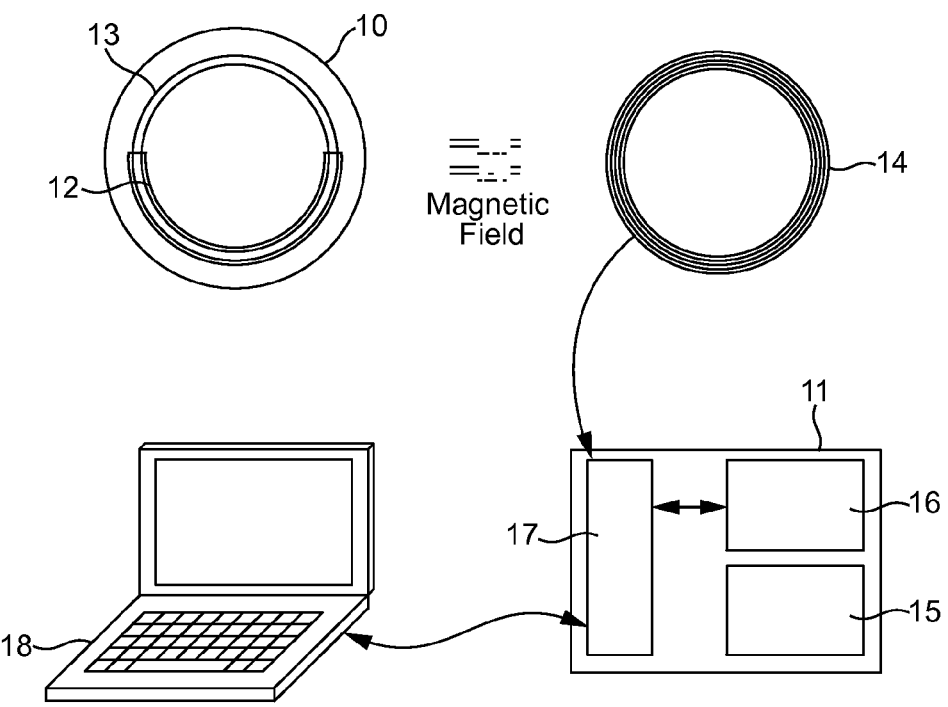
FIG. 2 is a schematic representation of the main components of a system comprising a contact lens device for the continuous monitoring of intraocular pressure in accordance with the present invention.

Referring to FIG. 2, one embodiment of the apparatus of the invention comprises two main components; a soft contact lens 10 and an external instrument 11. While dimensions may vary, in this embodiment the contact lens has a diameter of 14-15 mm and thickness that ranges between 120 μm (along the edge) and 280 μm (at the central region). It is made of soft silicone hydrogel material with Young's modulus, E, of 0.30 MPa and oxygen permeability of over $60 \times 10^{-11}$ $cm^2$ $mL_{O_2}/(s\ mL\ mm_{Hg})$, to ensure comfort of use over periods over 24 hours, and to enable fitting on corneas with different sizes and curvatures. The central zone with 6.0 mm diameter is free of any obstruction to enable clear vision during use. The lens is be worn in a similar fashion to normal contact lenses on a daily or extended-wear basis.

The contact lens has a circumferential pressure transducer 12 designed to detect small changes in intraocular pressure (IOP) and transmit them wirelessly to the external instrument 11. Communication between the contact lens (CL) and the external instrument is through a magnetic field generated by and between a respondent coil 13 embedded on the CL and an exciter coil 14 positioned a small distance in front of the monitored eye—e.g. on a pair of glasses or goggles during day use or a face mask for night use. The exciter coil 14 is connected to the external instrument 11, which will be designed to be small and light enough to fit on the arms of glasses or be supported on the side of the user's face using non allergic medical tape or be capable of being placed in a convenient pocket.

The external instrument 11 includes a power source 15, such as a battery, to power the exciter coil, generate the magnetic field and use it to transmit IOP signals back to the instrument. The instrument has a data storage unit 16 to store the IOP signals recorded over a period of at least 24 hours, a communication unit 17 to enable download of IOP measurements onto a personal computer 18 or other processor, a programmed hardware chip to control the operation of the instrument including storing and acting on instructions on when and for how long to take IOP measurements, to apply IOP corrections based on corneal stiffness estimates and to download the IOP readings when required.

Example 2

Figure 3:
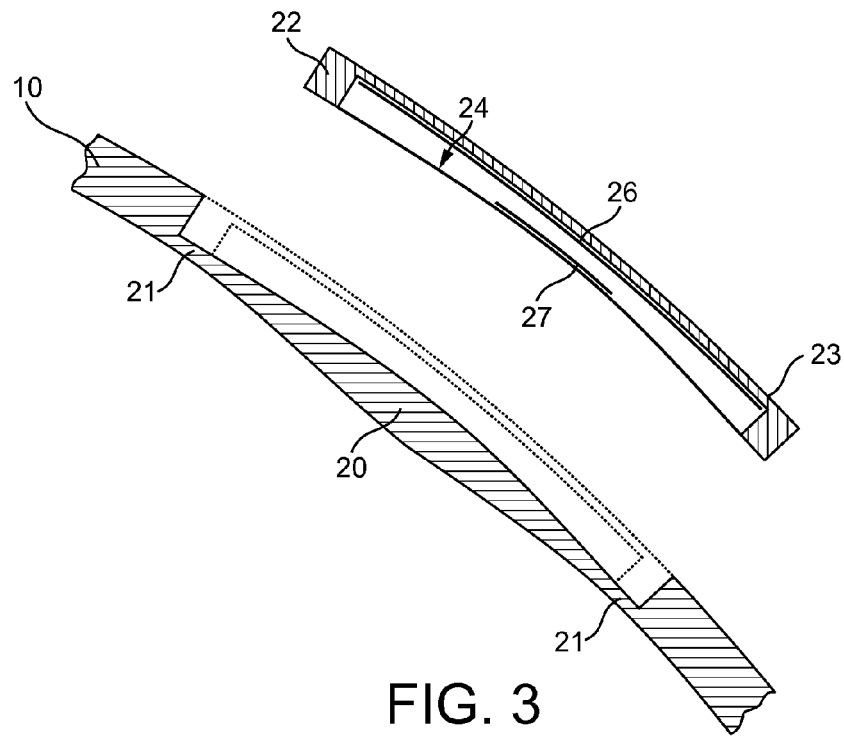
FIG. 3 is an exploded cross-sectional view part of the pressure sensor area of a device of the present invention.
Figure 4:
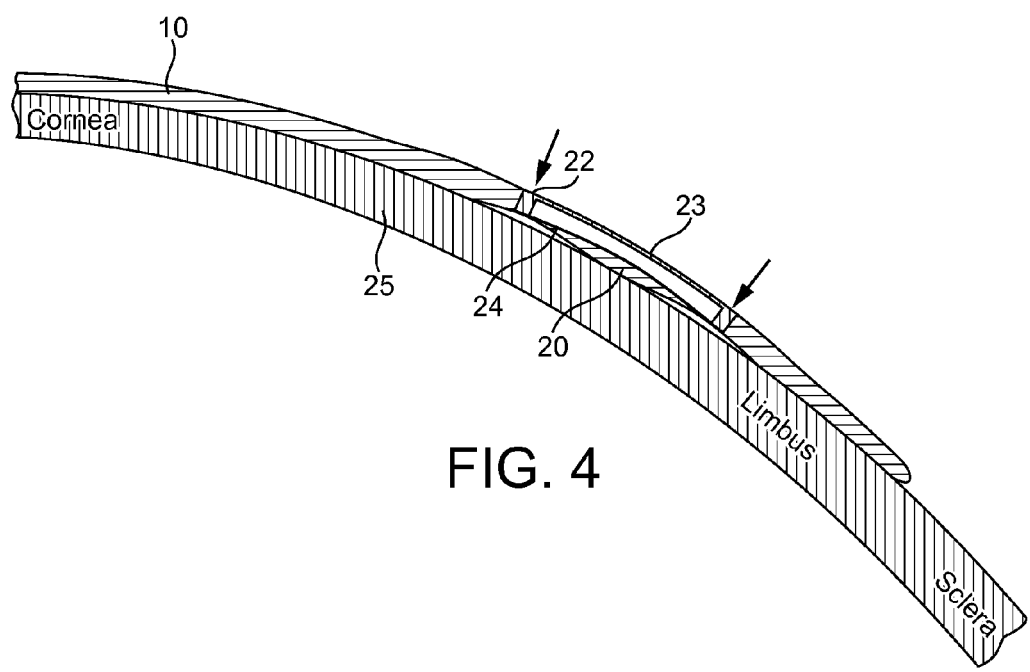
FIG. 4 is a cross-section through part of a device of the invention showing the pressure sensor part including the rigid bridge and the diaphragm.

Referring to FIGS. 3 & 4 details of the pressure sensor design will now be described. This pressure sensor has been found to produce stronger IOP signals, be more reliable and stable in operation in response to eye movement and tear film quality than previous designs. The design is based on indenting the cornea using eyelid pressure and correlating the resulting reactive deformation of the contact lens to the intraocular pressure (IOP). The design involves a modification of a soft contact lens 10 within a zone with typical dimensions of 7 mm internal diameter and 2.5 mm width. The profile in this zone is shaped as shown in FIG. 3, with a protruded part 20 that has weakened (thinner) peripheral regions 21. The space above the protruded part is covered with a relatively stiff bridge 22—formed by a ring of relatively stiff material with an elastic modulus of typically approximately 1 GPa, and a top surface 23 that matches the lens's anterior profile, and provides a smooth continuation thereof. FIG. 3 shows the bridge 22 separate from the lens 10. The position of the bridge when fitted onto the lens in use is shown by the dotted lines.

Along its inner edges, the rigid bridge 22 is firmly connected to a diaphragm 24 of softer material with a Young's modulus of typically approximately 1 to 40 MPa, depending on thickness. The connection between the rigid bridge 22 and the diaphragm 24 may advantageously be tight to ensure no moisture leakage during the extended wear of the contact lens 10.

On the upper surface of the diaphragm 24 is mounted a thin, electrically conducting, metal membrane 27. On the lower surface of the bridge 22 is a second thin, electrically conducting metal membrane 26. The metal membranes 26 and 27 are separated by an air gap, which acts as a dielectric, such that the metal membranes 26, 27 can function as the plates of a very low capacitance capacitor (typically of the order of pico-Farads).

The rigid bridge member 22 and the diaphragm 24 perform a number of desirable functions in the operation of the contact lens, as illustrated in FIG. 4. First, the bridge member collects the distributed eyelid pressure (denoted by the solid arrows in the Figure) applied over the surface 23 during blinking or other closing of the eyelids and transforms it into two concentrated forces acting along the periphery 21 of the protruded part. Applying these forces (without an intervening diaphragm) directly to the soft material of the contact lens (with low Young's modulus) would cause concentrated deformation at the periphery 21 of the protruded part 20 rather than causing the protruded part 20 to indent the cornea 25. For this reason, the diaphragm 24 is used to act as a stiffening membrane that uses the concentrated eyelid pressure to push the protruded part 20 against the cornea 25 and with the progress of the indentation process, the diaphragm 24 also deforms (because of the resistance offered by the cornea and IOP to indentation) and moves toward the internal surface of the bridge member 22. During this process, the distance between the internal surfaces of the bridge member 22, and the diaphragm 24, and hence the distance between conducting membranes 26 & 27, decreases, which has the effect of altering the capacitance thereof. The change in capacitance is detectable and, by virtue of a previously performed calibration, can be related to the value of the IOP.

The protruding portion of the lens will typically (but not necessarily) be substantially co-extensive with the pressure sensor.

If the recess or cavity section of the lens is circular, and so too is the bridge member located within it, then the rotational position of the lens on the eye of the subject should be largely irrelevant. This simplifies construction of the lens and accordingly represents a preferred embodiment.

If however the recess or cavity section, and associated bridge member located therein, are arcuate, then it will normally be desirable to include stabilising features in the design of the lens, to keep the lens in the required rotational position. Stabilising features are well-known and include "wedges" and the like, formed on the front surface of the lens.

In general, for lenses having an arcuate recess or cavity section and a correspondingly arcuate bridge member located therein, the arcuate section/bridge member will preferably mainly or wholly be at the lower half of the lens when worn by a subject i.e. between "2 o'clock" and "10 o'clock", more preferably between "3 o'clock" and "9 o'clock". In this rotational position, relative to the eye, the upper eye lid will press over most of the active pressure-sensing portion of the lens and exert maximal pressure thereon, thus increasing the sensitivity of the device.

The contact lens could in theory be a corrective lens, with an optical power intended to ameliorate a vision defect in a subject. More preferably however the lens will be planar and non-corrective.

Figure 5:
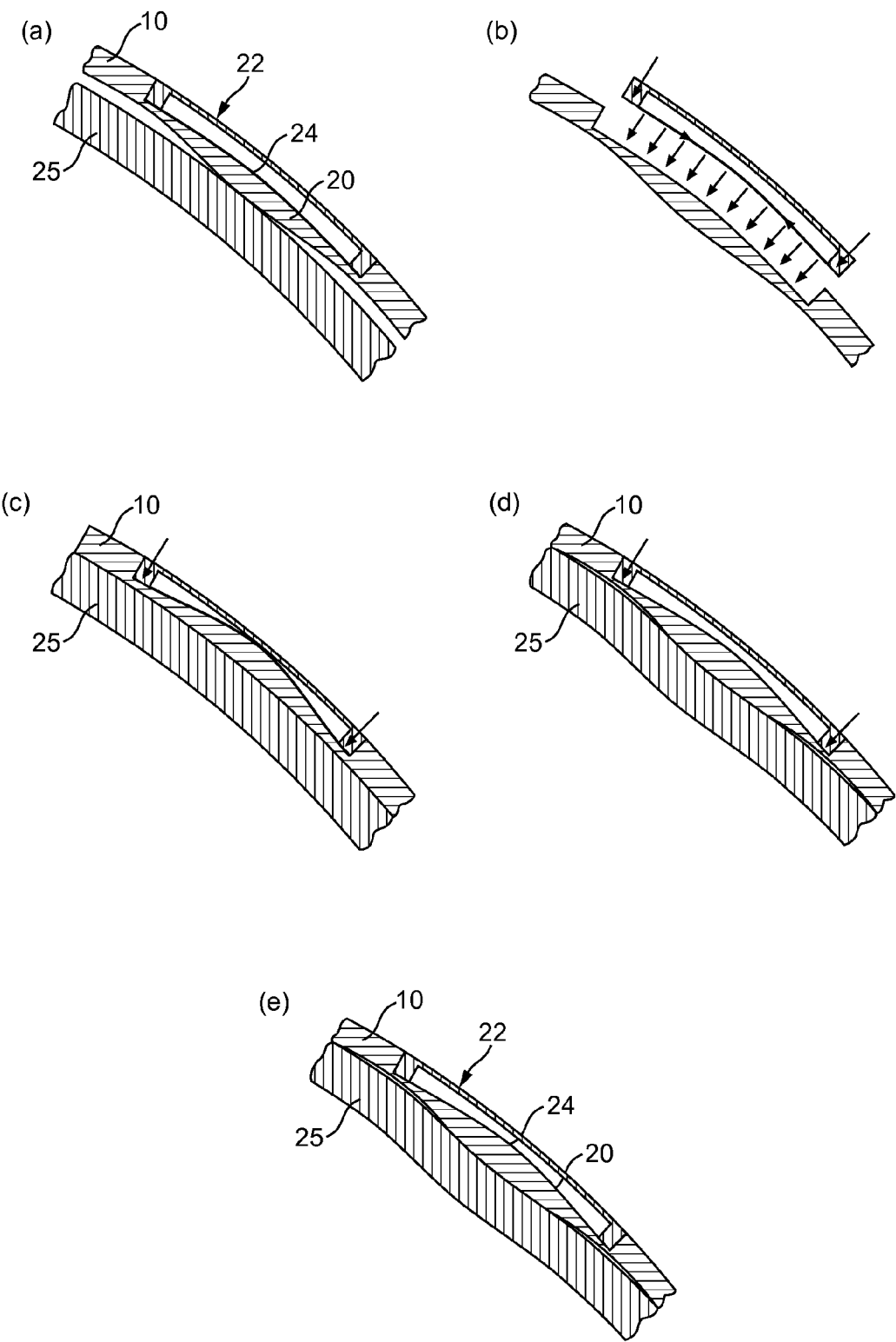
FIGS. 5 (a)-(e) are cross-sectional views showing deformation of a protruded part of the lens in cases with or without the diaphragm.

The stiffness of the diaphram 24 is an important parameter in the design of the contact lens. Referring to FIGS. 5a-5e, if formed with too high stiffness, (as shown in FIG. 5e), the diaphram 24 will push the protruded part of the lens to indent the cornea, but it will not deform enough during this process to register any variation in corneal resistance caused by variations in IOP. On the other hand, if the diaphragm has too low stiffness, it will allow the protruded part to flatten on the surface of the cornea rather than indenting it. This is further illustrated with particular reference to FIGS. 5c and 5d which show, in 5c, that without the diaphragm 24, or with a diaphragm with too low stiffness, the protruded part 20 deforms without significant cornea indentation while, in 5d, with the diaphragm 24 of appropriate stiffness, both the diaphragm and the cornea 25 deform under eyelid pressure.

Example 3

Figure 6:
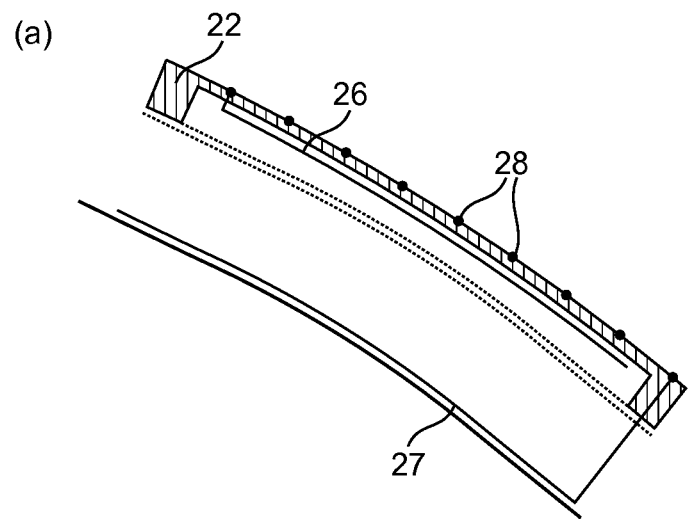
FIGS. 6 (a) & (b) are respectively a cross-section and plan view of a rigid ring of a contact lens device showing the metal membranes fixed on the diaphragm and the rigid ring.
Figure 6:
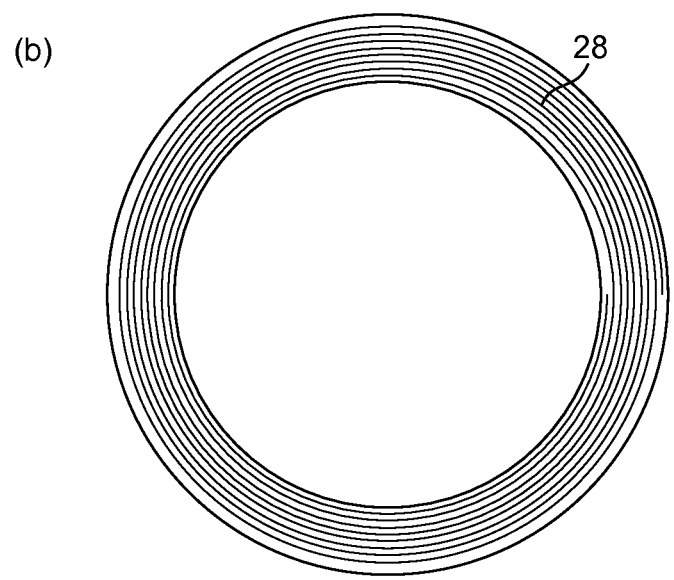
Figure 7:
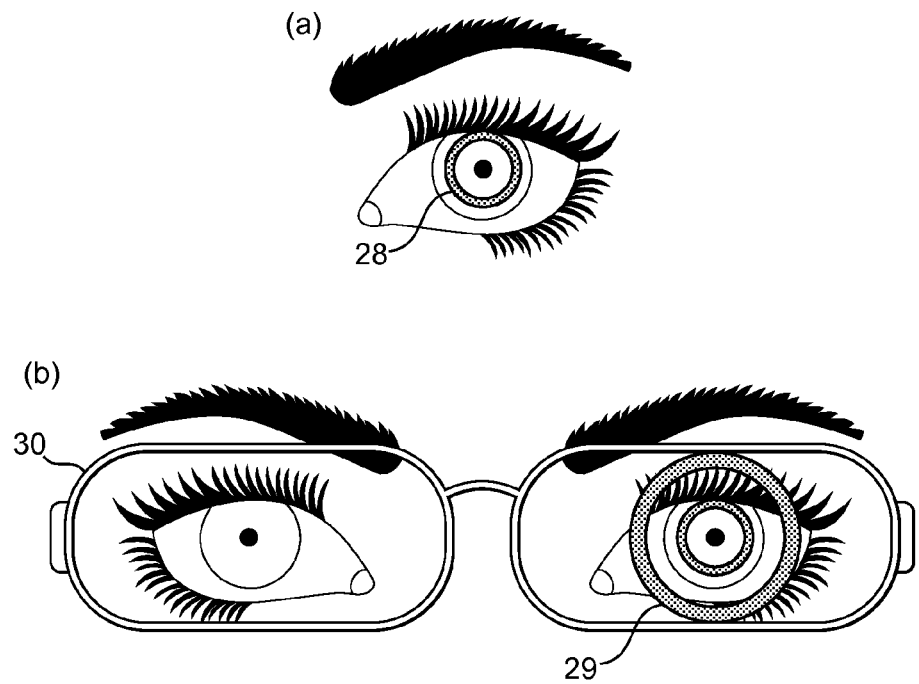
FIGS. 7 (a) & (b) are respectively front views of a respondent coil on a contact lens and an exciter coil placed on spectacles (with corrective lenses or otherwise)

Referring now to FIGS. 6 *a* & *b*, the deformation of the diaphragm 24 is measured using a capacitor system involving two thin metal membranes 26, 27 fixed to the internal surfaces of the bridge member and the diaphragm, respectively. As the diaphragm deforms, the distance between the two metal membranes changes, leading to a change in the capacitance of the capacitor formed by the two membranes. This in turn affects the resonant frequency of the oscillator formed by the combination of the capacitance of the capacitor and the inductance of the responder coil. In order to power the circuit of the capacitor and record the resonant frequency values, a magnetic field is formed between and encompassing a responder coil 28 embedded on the external surface of the bridge member 22 and an exciter coil 29 to be positioned externally close to the eye, e.g. on a pair of spectacles 30 (FIG. 7). By energising the exciter coil with an alternating current, an alternating current will be created in the responder coil. Should the frequency of the alternating current in the exciter coil correspond to the resonant frequency of the responder coil and capacitor circuit, this will be detectable e.g. by measurement of the current used to energise the exciter coil. At the resonant frequency of the oscillator, there is a peak in the amplitude of the alternating current flowing through the exciter coil circuit. As the resonant frequency is directly proportional to the capacitance of the capacitor, the capacitance value may be determined by energising the exciter coil with a number of different frequencies, each time determining the current used.

The exciter coil 29 will be larger in size than the responder coil 28, and will be placed on a transparent plastic membrane, which can be adhered to the back-surface of spectacles or a face mask during day and night use, respectively. The exciter coil 29 will be connected with an insulated thin cable to the external instrument 11 for power and transmission of IOP signals.

Figure 8:
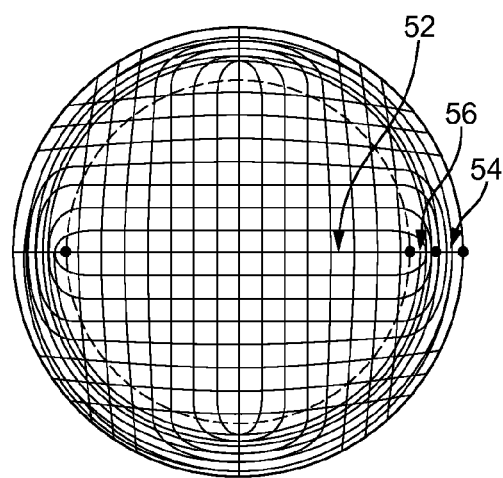
FIG. 8 is a schematic illustration of the changes in collagen fibre orientation from meridian in the corneal central region to circumferential at the limbus or the corneo-scleral intersection.

The pressure sensor is placed within an annular zone with inside and outside diameters of approximately 7 and 11 mm, respectively. In addition to enabling clear vision through the the 6 mm-diameter central region, the placement of the sensor in this zone benefits from a particular feature of corneal micro-structure. As shown in FIG. 8, while the central cornea (52) is known to have preferential orientation of collagen fibres in the vertical and horizontal meridian directions, the fibres change direction to become circumferential at the limbus (54). The transition zone (56), which has a diameter between 7 and 11 mm, is where the fibres change direction. This zone (56) has been found to possess lower stiffness values compared with surrounding regions, and as a result would be expected to deform more under the eyelid pressure action and hence provide stronger IOP signals, making the apparatus more sensitive.

IOP measurement techniques (including the present device) rely on applying a mechanical force to the cornea and calibrating the deformation response to the value of IOP. This process implies that the IOP readings will inevitably be affected by variations in corneal resistance to deformation (or stiffness), which in turn is influenced by parameters such as corneal thickness, curvature and age. Without proper consideration of the effect of stiffness on IOP readings, the device measurements will be inaccurate and calibration may become necessary for every patient.

Figure 9:
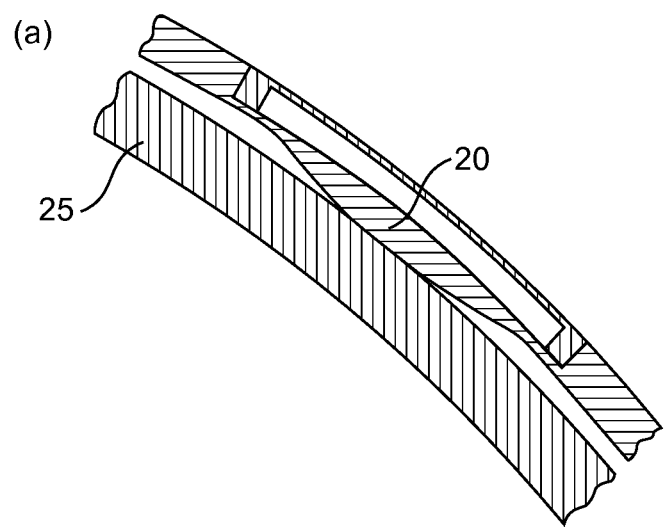
FIGS. 9 (a) & (b) are respectively cross-sectional views of the profile of a protruded part of a contact lens in un-modified form and a modified form arranged to produce different corneal deformation behaviour.
Figure 9:
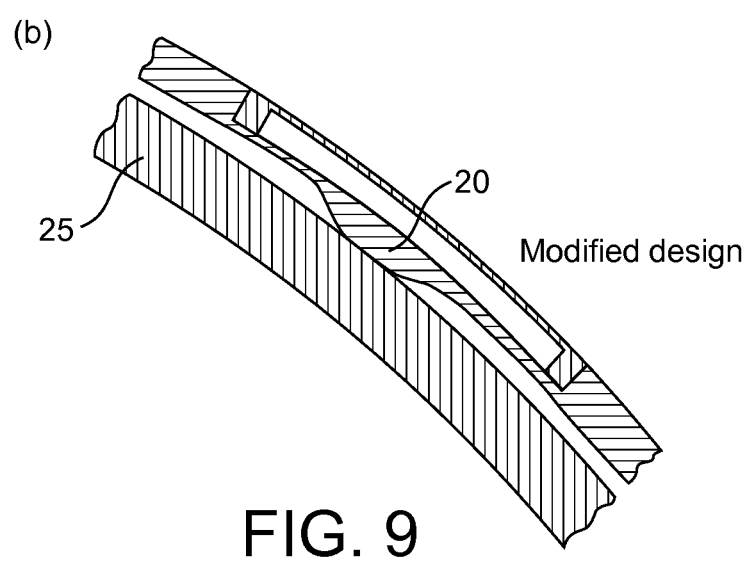

The device has been configured to obtain a direct measure of corneal stiffness and its effect on IOP measurements. The technology is based on the use of a contact lens with similar design to that previously proposed, but with a different protruded part profile (more steeply sloped) as can be seen in FIG. 9(*b*). The difference in profile will lead to a different interaction between IOP and corneal mechanical resistance (stiffness) to the indentation effect of the protruded part. Appropriate numerical analysis will allow the indentation action of the lens design to be assessed and correlated to the level of corneal stiffness and its effect on IOP measurements.

Example 4

Figure 10:
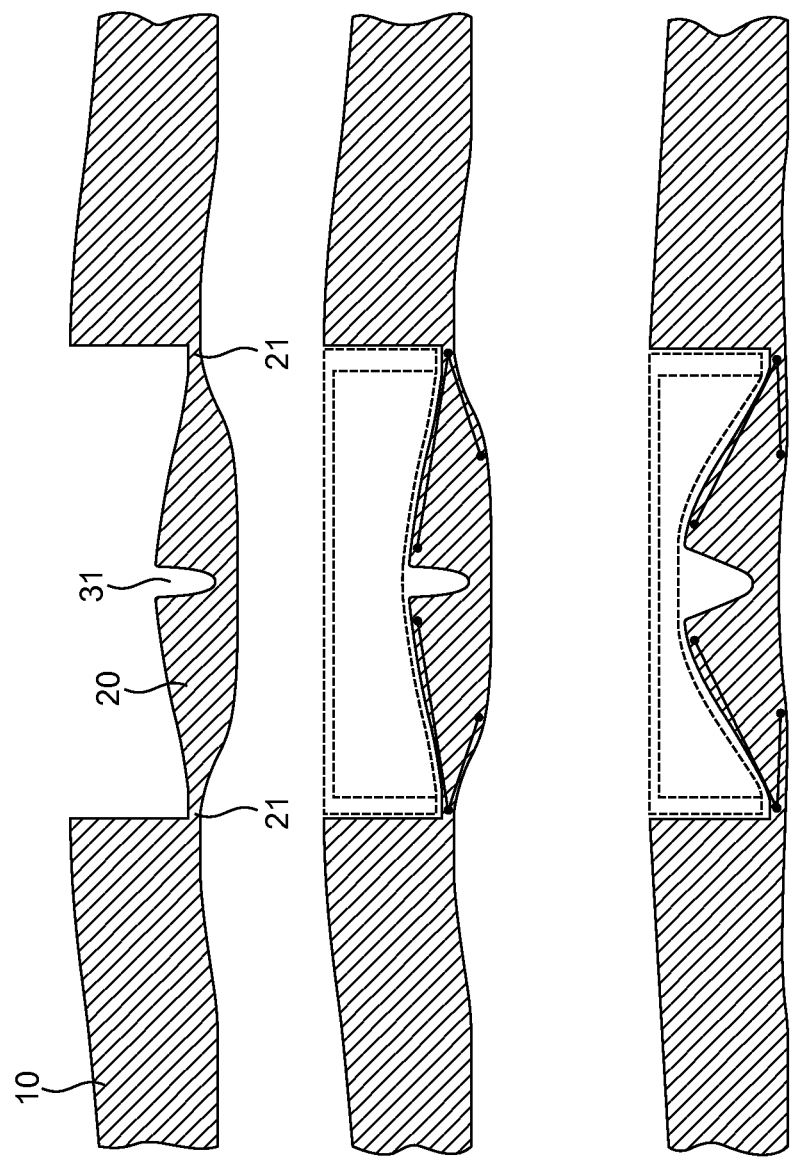
FIG. 10 is a diagrammatic representation of a further embodiment of a contact lens of the present invention in which the middle section of the protruded part of the lens has a weakened point.

An alternative arrangement of the contact lens 10 is shown in FIG. 10. In this embodiment the protruded part 20 of the lens 10 has a weakened middle point 31 which effectively introduces a third hinge at the middle of the protruded part to allow easier deformation and rotation about the hinges formed by the weakened edges 21. The protruded part also has a wide base such that under eyelid pressure, the two halves of the protruded part would rotate around the two edges of the base and produce large deformation at the central region of the protruded part. This arrangement may therefore be used to magnify the signal strength produced by changes in IOP.

Figure 11:
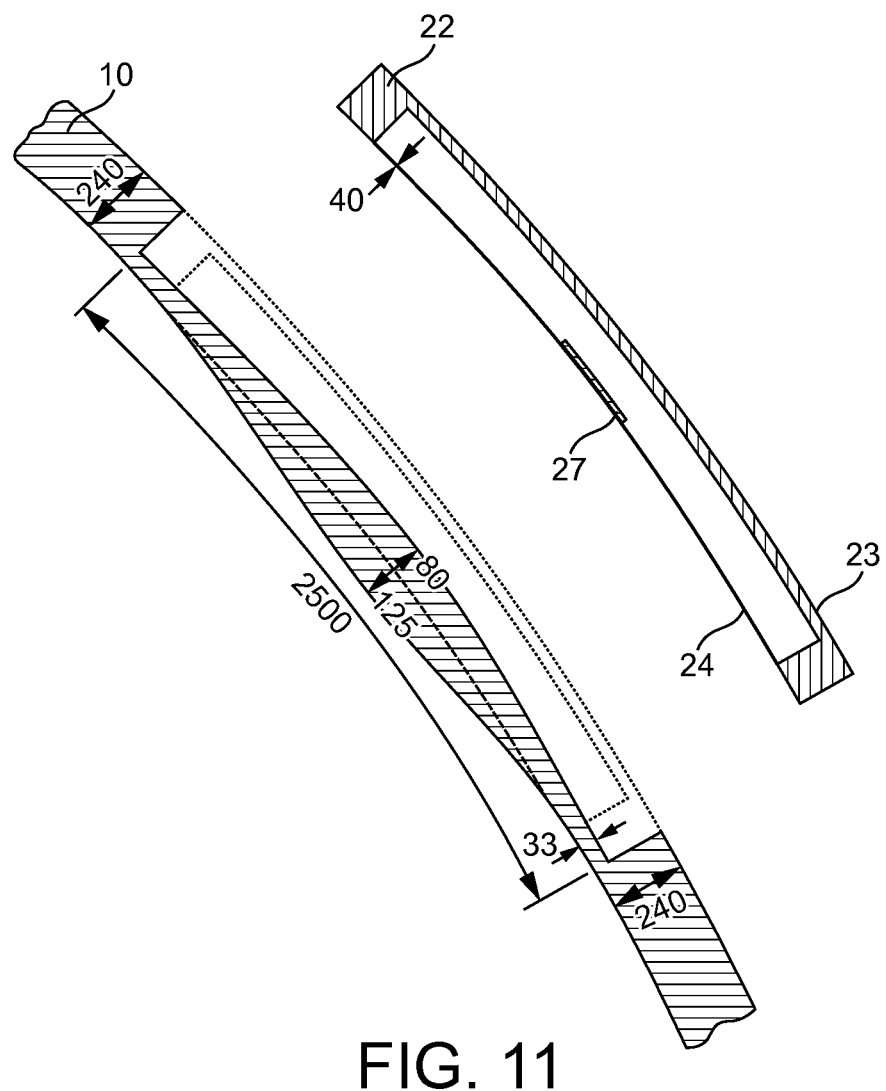
FIG. 11 is a view corresponding to FIG. 3 in which typical dimensions in microns have been included.

Typical dimensions, all in microns, of the various components of the contact lens device are shown in FIG. 11.

Example 5

Figure 12:
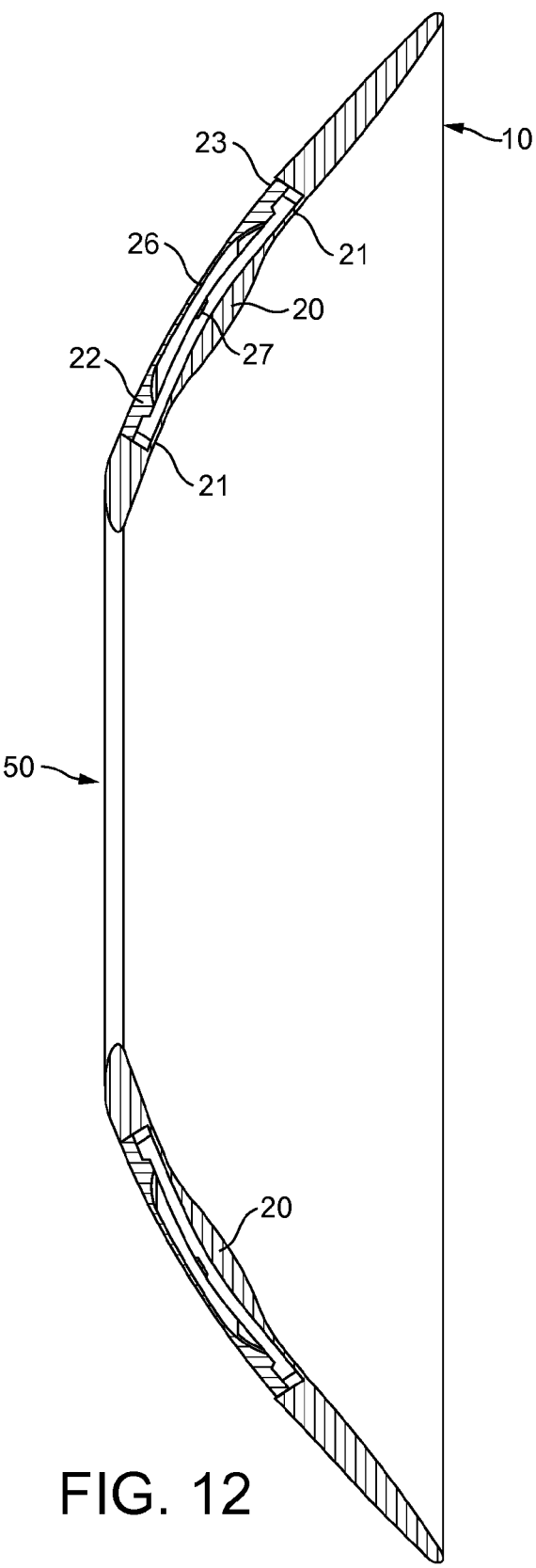
FIG. 12 is a sectional view of a further embodiment of a contact lens device in accordance with the invention.
Figure 13:
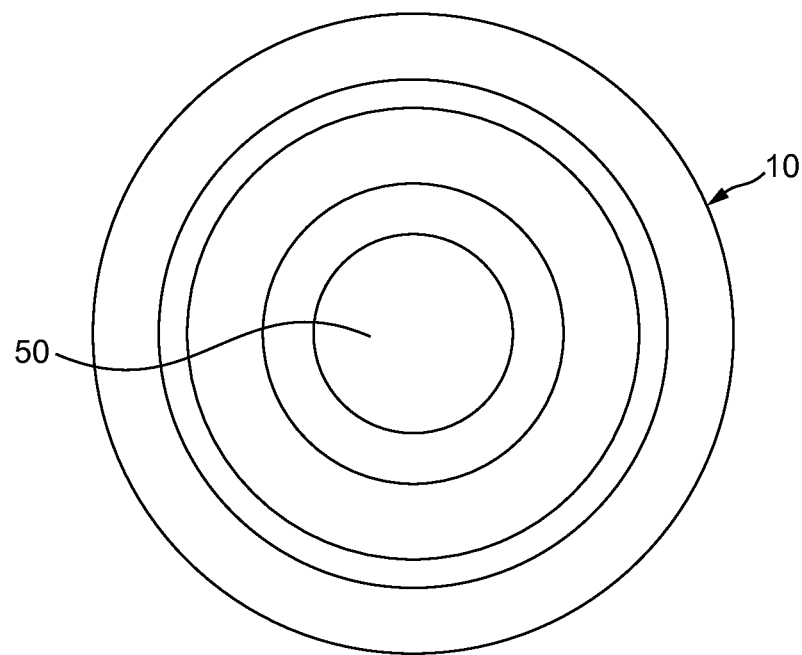
FIG. 13 is a plan view, to a different scale, of the embodiment shown in FIG. 12.

A different embodiment of the device of the invention is illustrated in FIGS. 12 & 13.

FIG. 12 is a mid-sectional view of the device. It is generally similar to the embodiment illustrated in FIGS. 3 and 4, and like parts are denoted by common reference numerals. Thus, the soft lens-like device 10 has an annular protruding portion 20 with thinner inner and outer peripheral regions 21. The protruding portion 20 is covered by a relatively stiff bridge 22, which has a top surface 23 which matches the lens's anterior profile to provide a smooth continuation thereof. Thin metal membranes 26 and 27 are provided, separated by an air gap which acts as a dielectric, so that the metal membranes 26 and 27 can function as the plates of a low capacitance capacitor.

The embodiment differs from that described previously, in that a circular central aperture 50 is formed in the device, as best seen in FIG. 13. A number of important advantages arise from the provision of an aperture:

(1) the device does not substantially impede or block the subject's unaided vision when the device is worn;
(2) the device does not inhibit the flow of oxygen to the cornea, which is especially important if the device is worn for long periods;
(3) the aperture permits the use of an applanation tonometer to take IOP readings whilst the device is in situ on the eye—the tip of the tonometer can pass through the aperture to contact the subject's cornea, thus enabling direct calibration of the device of the invention.

Example 6

Whilst the device of the invention relies on eyelid pressure during blinking, or eye closure in sleep, to produce microindents of the cornea and trigger IOP readings, it is desirable that the IOP measurements are as independent as possible from the level of eyelid pressure. This is important since the eyelid pressure is reported to decrease with advancing age.

A device in accordance with the invention was assessed and found to produce IOP signals that remained substantially stable with reductions in eyelid pressure from its highest level of 8 mmHg down to 2.5 mmHg. This was achieved by selecting a depth of the protruded part that made it possible to close the gaps under the weakened ends using 2.5 mmHg eyelid pressure. Any increase in eyelid pressure above this level (up to 8 mmHg and beyond) would only press on the lens and the cornea while they are in complete contact and would not change the deformation of the diaphragm or the IOP signals.

Figure 14:
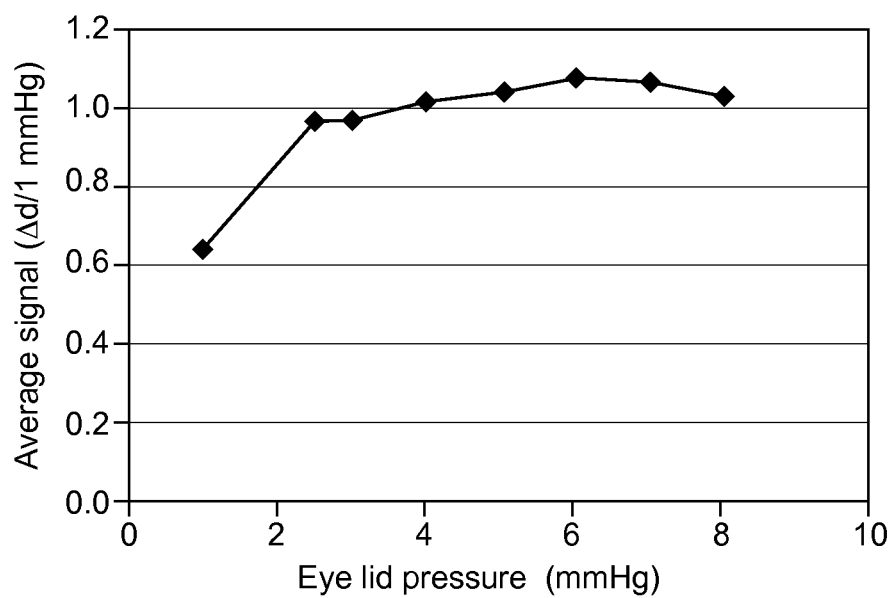
FIG. 14 is a graph of average signal ($\Delta d/1$ mm Hg) against eyelid pressure (mmHg).

The results of the analysis are shown in FIG. 14.

This technology of the present invention has the advantage of measuring corneal stiffness directly instead of the factors affecting it (thickness, curvature, age, etc.) as has been done previously.

Throughout the description and claims of this specification, the words "comprise" and "contain" and variations of them mean "including but not limited to", and they are not intended to (and do not) exclude other components integers or steps. Throughout the description and claims of this specification, the singular encompasses the plural unless the context requires otherwise. In particular, where the indefinite article is used, the specification is to be understood as contemplating plurality as well as singularity, unless the context requires otherwise.

Features, integers and characteristics described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

The reader's attention is directed to all papers and documents which are filed concurrently with or previous to this specification in connection with this application and which are open to public inspection with this specification, and the contents of all such papers and documents are incorporated herein by reference.

What is claimed is:

1. A device adapted to measure intraocular pressure comprising:
    a corneal contact lens having a pressure sensor mounted in a recess or cavity in the contact lens, and wherein the contact lens has a back surface which is formed so as to protrude in a desired portion beyond the profile of the adjacent part of the lens and is configured to press against the cornea, which protruding portion experiences a reactive deformation which is detected directly or indirectly by the pressure sensor,
    wherein the contact lens is adapted and configured such that the pressure sensor, when in situ on an eye of a subject, overlies the transition zone of the cornea of the eye.

2. A device according to claim 1, wherein the protruding portion experiences a reactive deformation when the eyelids are closed but not when the eyelids are open.

3. A device according to claim 1, wherein the protruding portion of the lens underlies the recess or cavity.

4. A device according to claim 1, wherein the recess or cavity is annular or arcuate.

5. A device according to claim 1, wherein the pressure sensor comprises a capacitor, the capacitance of which is altered by the reactive deformation experienced by the protruding portion of the contact lens.

6. A device according to claim 1, wherein there is provided a stiff "bridge" member accommodated within the recess or cavity, which "bridge" member has an elastic modulus which is greater than that of the contact lens material.

7. A device according to claim 6, wherein the pressure sensor comprises a capacitor, one of the plates of which is attached to the stiff bridge member.

8. A device according to claim 6, wherein the pressure sensor comprises a diaphragm which overlies the protruding portion of the lens, the diaphragm being formed of a material which has an elastic modulus which is intermediate between that of the contact lens material and that of the stiff bridge member.

9. A device according to claim 8, wherein the pressure sensor comprises a capacitor, one of the plates of which is attached to the diaphragm.

10. A device according to claim 1, wherein the protruding portion is joined to the rest of the contact lens by one or more weakened areas which are thinner than the main body of the lens.

11. A device according to claim 10, wherein there is provided a stiff "bridge" member accommodated within the recess or cavity, which "bridge" member has an elastic modulus which is greater than that of the contact lens material, and wherein the stiff "bridge" portion has legs or supports which act on the one or more weakened areas, such that pressure on the bridge from the eyelid is applied to the weakened areas, to push the protruding portion of the lens against the cornea.

12. A device according to claim 1, wherein the contact lens further is comprises a coil of electrically conducting material.

13. A device according to claim 1, wherein the protruding portion and/or the pressure sensor is configured and located so as to overlie the transitional zone of the cornea and not to extend therebeyond.

14. A device according to claim 1, comprising a central aperture formed in the contact lens.

15. A device according to claim 14, wherein the central aperture is essentially circular.

16. A device according to claim 14, wherein the aperture is of sufficient dimension to allow the tip of an applanation tonometer to contact the cornea.

17. A method of directly calibrating a device in accordance with claim 16, the method comprising the steps of:
    (a) introducing onto the eye of a subject the device in accordance with claim 16;
    (b) obtaining at least one measurement using said device;
    (c) using an applanation tonometer to obtain one or more readings of IOP or OPA in the subject's eye whilst the device of the invention is in situ on the eye, by passing the tip of the applanation tonometer through the aperture, provided in the device, far enough to contact the cornea and obtain one or more readings of IOP or OPA; and
    (d) directly calibrating the device of the invention using the measurement obtained in step (b) and the one or more readings of IOP or OPA obtained in step (c).

18. A method according to claim 17, wherein steps (b) and (c) are performed, in either order, within 3 minutes of each other.

19. A device according to claim 1, wherein the transition zone of the cornea is an annular region adjacent a central region of the cornea located between the limbus and the central region of the cornea.

20. A device according to claim 1, wherein the transition zone of the cornea is an annular region adjacent a central region of the cornea, the annular region having an inner diameter of 7 mm and an outer diameter of 11 mm.

21. A device according to claim 1, wherein the transition zone of the cornea is a region in which collagen fibers change direction from vertical and horizontal directions to a circumferential direction.

22. Apparatus for measuring IOP in a subject comprising a device according to claim 1, in combination with spectacles or an eye mask having an exciter coil which induces an emf in a respondent coil located on or in the contact lens.

23. Apparatus according to claim 22, wherein the exciter coil is positioned on the rear surface of the lens of the spectacles, the spectacles preferably comprising one or two corrective lenses.

24. Apparatus according to claim 22, wherein the spectacles or eye mask comprises, as an integral component, a source of electrical power which drives the exciter coil.

25. Apparatus according to claim 22, wherein the exciter coil is operated with an alternating current, the frequency of which is cycled over a desired range.

26. Apparatus according to claim 22, wherein the apparatus can monitor and record IOP over a period of at least 24 hours, the apparatus further comprising: a digital signal processing unit and a data storage unit.

27. Apparatus according to claim 26, further comprising one or more of the following: a signal generator unit, a user interface, and a data communication unit for transferring data via a wire or wirelessly.

28. Apparatus according to claim 26, adapted for measuring and/or monitoring OPA.

29. Apparatus according to claim 22, wherein all of the necessary components are provided, in combination, on the contact lens or the spectacles or eye mask.

30. Apparatus according to claim 22, wherein the exciter coil is positioned on the rear surface of the lens of the spectacles, the spectacles comprising one or two corrective lenses.

31. A method of determining the IOP or OPA in the eye of a subject, the method comprising the steps of:
    (a) introducing onto the eye of the subject a device in accordance with claim 1;
    (b) obtaining at least one measurement using the device; and
    (c) using the at least one measurement from step (b) to determine the IOP or OPA of the subject's eye.

32. A method according to claim 31, wherein step (b) comprises obtaining a plurality of measurements.

33. A method according to claim 32, wherein the plurality of measurements are obtained over a period of at least 12 hours.

34. A method according to claim 31, wherein the at least one measurement in a period in which the subject is asleep.

35. A method according to claim 31, further comprising the step of diagnosing the existence of glaucoma in the subject's eye, based on the determined IOP or OPA.

36. A method of measuring or estimating corneal stiffness, the method comprising the steps of:
    (a) introducing onto the eye of a subject a first device in accordance with claim 1, and obtaining a first data set relating to IOP in the subject's eye;
    (b) removing the first device and introducing onto the same eye a second device in accordance with claim 1, the second device differing in some relevant characteristic, in a known manner, from the first device, and obtaining a second data set relating to IOP in the subject's eye; and
    (c) comparing the first and second data sets to allow a measurement or estimation of the corneal stiffness of the subject's eye.

37. A method according to claim 36 wherein the second device differs from the first device in the steepness of curvature of the protruding portion of the contact lens.

38. (Withdrawn - Currently Amended) A method according to claim 36, wherein the first device has a protruding portion with a greater steepness of curvature than that of the second device, and where the first device is worn for less than 10 minutes and the second device is worn for 24 hours or more.

39. A stiff bridge member for use in a device in accordance with claim 1, the bridge member being circular or arcuate.

40. A bridge member according to claim 39, further comprising any one or more of the following:
    a respondent coil;
    a first conducting element, acting as a first capacitor plate;
    a diaphragm, having an elastic modulus intermediate in value between that of the bridge member and that of a soft contact lens with which the bridge member is to be associated; and
    a second conducting element, acting as a second capacitor plate.

41. A bridge member according to claim 39, further comprising any one or more of the following:
    a respondent coil embedded in the bridge member;
    a first conducting element, acting as a first capacitor plate;
    a diaphragm, having an elastic modulus intermediate in value between that of the bridge member and that of a soft contact lens with which the bridge member is to be associated; and
    a second conducting element, acting as a second capacitor plate located on the diaphragm.

42. A stiff bridge member for use in a device in accordance with claim 1, the bridge member being circular or arcuate having an elastic modulus in the range 300 MPa to 3 GPa.

* * * * *